United States Patent [19]

Morihara et al.

[11] 4,400,465

[45] * Aug. 23, 1983

[54] SEMI-SYNTHESIS OF HUMAN INSULIN

[75] Inventors: Kazuyuki Morihara; Tatsushi Oka, both of Osaka; Hiroshige Tsuzuki, Hirakata, all of Japan

[73] Assignee: Shionogi & Co., Ltd., Osaka, Japan

[*] Notice: The portion of the term of this patent subsequent to Mar. 16, 1999 has been disclaimed.

[21] Appl. No.: 336,071

[22] Filed: Dec. 31, 1981

Related U.S. Application Data

[62] Division of Ser. No. 138,514, Apr. 9, 1980, Pat. No. 4,320,196.

[30] Foreign Application Priority Data

Apr. 13, 1979 [JP] Japan ................................. 54-45710

[51] Int. Cl.³ ...................... C12P 21/04; C12R 1/025; C12R 1/465; C12R 1/54
[52] U.S. Cl. ..................................... 435/71; 435/896; 435/886; 435/824
[58] Field of Search ...................... 435/68, 69, 70, 71, 435/824, 896, 886; 424/178

[56] References Cited

U.S. PATENT DOCUMENTS

| | | | |
|---|---|---|---|
| 3,276,961 | 10/1966 | Bodanszky et al. | 424/178 |
| 3,903,068 | 2/1975 | Ruttenberg | 260/112.7 |
| 4,320,196 | 3/1982 | Morihara et al. | 435/70 |

OTHER PUBLICATIONS

Yoshida et al., FEBS Letters, 15(2), 129–132, (1971).
Schmitt et al., Hoppe-Seyler's Z. Physiol. Chem., 359, 799–802, (1978).
Obermeier et al., Hoppe-Seyler's Z. Physiol. Chem., 357, 759–767, (1976).
Inouye et al., JACS, 101, 751–752, (1979).
Morihara et al., Nature, 280, 412–413, (1979).
Morihara et al., Arch. Biochem. Biophys., 126, 971–973, (1968).

Primary Examiner—Esther M. Kepplinger
Attorney, Agent, or Firm—Wenderoth, Lind & Ponack

[57] ABSTRACT

A process for preparing a B30-threonine-insulin which comprising reacting a des-B30-insulin with an excess amount of threonine derivative in the presence of an enzyme specifically acting on the basic-amino-acid carbonyl in peptide bondings.

20 Claims, No Drawings

SEMI-SYNTHESIS OF HUMAN INSULIN

This application is a division of Ser. No. 138,514, filed Apr. 9, 1980, now U.S. Pat. No. 4,320,196.

This invention relates to a semi-synthesis of human insulin. More particularly, it consists of an enzymatic synthesis of a B30-threonine-insulin including human insulin. The synthesis is effected to by reacting a des-B30-insulin with an excess amount of threonine derivative in the presence of an enzyme specifically acting on the basic-amino-acid carbonyl in peptide bondings and removing any protecting group of the threonine to yield a B30-threonine insulin.

Insulin is an indispensable medicament for treatment of diabetes. Bovine and porcine insulins are commercially available at present. These insulins are, however, different from human insulin in a few amino acid components, which cause formation of antibody in patients. The antibody is known to decrease the effectiveness of further insulin treatment. Therefore, human insulin is favoured and its commercial availability has been eagerly desired. Human insulin is different from other animal insulin in amino acid components at the positions 8, 9, and 10 of the A chain and at the position 30 of the B chain. This invention provides a process to substitute the amino acid at the 30 position of the B chain of an animal insulin with L-threonine. Accordingly, human insulin can be easily prepared by the process of this invention using porcine insulin as starting material. Porcine insulin is different from human insulin in the amino acid at the B30 position. Thus-obtained human insulin is favourably used for treatment of diabetic patients. Further, this invention provides other B30-threonine-insulins starting from other animal insulins. The resultant insulins are different from human insulin in amino acids at 8, 9, and 10 positions of the A chain and can be used as reagents to test antigenicity and as medicament for diabetes.

Human insulin was chemically prepared by M. A. Ruttenberg as shown in U.S. Pat. No. 3,903,068 and by R. Obermeier et al. as described in Hoppe-Seyler's Z. Physiol. Chem., 357, 759–767 (1976). These processes comprise condensation of a desoctapeptide-(B23-30)-porcine insulin with a synthetic octapeptide corresponding to positions B23-30 of human insulin. The former process, however, includes alkaline hydrolysis which is accompanied by adverse side-reactions. The latter process is also a non-specific reaction which brings about many side-reactions and requires complicated purification procedures. Therefore, these processes cannot be applied on an industrial scale.

M. Bodanszky et al. provide a process for preparing human insulin in U.S. Pat. No. 3,276,961 wherein human insulin was prepared from other animal insulins by an action of an enzyme such as carboxypeptidase A and trypsin in the presence of threonine. This process is not likely to product human insulin because trypsin and carboxypeptidase A hydrolyze not only the peptide bond of lysyl-alanine (B29-B30) but also the other positions in insulin under the condition described there. Trypsin preferentially hydrolyzes the peptide bond of arginyl-glycine (B22-B23) rather than that of lysyl-alanine (B29-B30). Meanwhile, carboxypeptidase A cannot release solely the alanine at the C-terminal of the B chain without liberating asparagine at the C-terminal of the A chain. A special condition, i.e. reacting in an ammonium hydrogen-carbonate buffer solution, is necessary to prevent the release of the asparagine. The condition was discovered in 1978 (Hoppe-Seyler's Z. Physiol. Chem., 359, 799–802 (1978)). Furthermore, peptide synthesis may hardly occur because the hydrolysis ratio is faster than the synthesis ration under this special condition.

Therefore, it is concluded that there has been no industrially available process for preparating human insulin until now.

This invention, however, can provide human insulin on an commercial scale. The process consists of enzymatic condensation of a des-B30-insulin with a L-threonine derivative. The process is different from any known process and has many advantages. It is a specific reaction not accompanied by any adverse side reaction such as racemization. Additionally, unreacted starting materials can be easily recovered without damage and can be reutilized. The process uses an excess amount of L-threonine derivative. The excess amount of the threonine derivative prevents the breakage of the carbonyl bond of the arginine at the 22 position of the B chain, although the bond usually split by trypsin. Accordingly, the protection of the arginine residue which is indispensable in usual enzymatic reaction is not necessary in this process.

The process comprises a reaction of a des-B30-insulin (noted as Compound II hereinafter) with an excess amount of L-threonine derivative (noted as Compound I hereinafter) in the presence of an enzyme specifically acting on the basic-amino-acid carbonyl in peptide bondings and further subjecting the product to deprotecting group reaction to yield a B30-threonine insulin.

Compound I is represented by the following formula:

wherein Thr is an L-threonine residue; $R^1$ is hydrogen or a hydroxy-protecting group; and $R^2$ is a carboxyl-protecting group.

Compound II can be prepared by reacting various animal insulins (e.g. pig, cattle, whale, sheep, rabbit, fish, monkey and the like) with carboxypeptidase A as disclosed by E. W. Schmitt et al. in Hoppe-Seyler's Z. Physiol. Chem. 359, 799 (1978). It is also prepared by using a protease produced by *Achromobacter lyticus*. The protease has a specificity to lysine and specifically splits the lysine carbonyl bond in peptide bondings. The isolation and characteristics are described by Masaki et al. in Agric. Biol. Chem., 42, 1443 (1978). The enzyme is called Protease I. The preparation des-B30-porcine insulin is disclosed in Biochem. Biophys. Res. Commun. 92, 396–402 (1980) and Japanese Patent Publication (Not-examined) No. 54-135789. Des-B30-insulins of other animals can be prepared in the same manner.

The hydroxy group of Compound I may be protected or not. Both the protected and unprotected can be subjected to the reaction. The protecting group to be used is selected from any hydroxy-protecting group generally used in peptide synthesis such as t-butyl, benzyl, acetyl and the like. The carboxyl group of Compound I has to be protected and any carboxyl-protecting group utilized in peptide synthesis can be employed. They are, for example, alkyl esters (e.g. t-butyl ester), aralkyl esters (e.g. benzyl ester), amide, substituted amides (e.g. anilide), salts (e.g. sodium) and so forth.

Protecting groups should be chosen considering the influence of the introduction and removal reactions to insulin because the reactions might result in denaturing or inactivation of insulin. If a hydroxy-protecting group and a carboxyl-protecting group of the threonine residue are suitably selected, one removal procedure is enough to remove both the protecting groups. Protecting groups used in peptide synthesis are detailed by M. Bodanszky et al. in Peptide Synthesis, the second edition (1976) published by John Wiley & Sons.

The enzyme used in the present process includes enzymes specifically acting on the basic-amino-acid carbonyl in peptide bondings which are obtainable from various plants and animals. They are, for example, trypsin, trypsin-like enzymes and the like. Tryspin-like enzymes are illustrated such as the protease isolated by Morihara et al. in Arch Biochiem. Biophys., 126, 971 (1968), which is produced by *Streptomyces fradiae* ATCC 3535, and the protease disclosed by Yoshida et al. in FEBS Lett., 15, 129 (1971), which is produced by *Streptomyces erythreus*. The enzyme to be used may be treated with tosyl-L-phenylalanine chloromethylketone (abbreviated TPCK hereinafter) to remove mixed enzymes such as chymotrypsin and chymotryspinlike enzyme.

The condensation of Compound I with Compound II is effected under suitable conditions for the peptide synthesis of the above enzymes.

The reaction is preferably effected at about pH 5 to 9, more preferably about pH 5 to 8, most preferably about pH 6 to 7. Reaction temperature is about 0° to 50° C., preferably about 20° to 40° C. It is desired that both concentrations of Compound I and Compound II are as high as possible. The preferable molar ratio of Compound I and Compound II is about 5:1 to 1000:1, especially about 25:1, to 200:1, about 20:1 to 100:1 being most favored.

Water-miscible organic solvents are preferably added to the reaction mixture. The addition of the organic solvent lowers the aqueous concentration of the reaction mixture resulting in prevention of reverse reaction, i.e. hydrolysis of product, and also remarkably increases the solubility of Compound I and Compound II. The organic solvents to be used are, for example, methanol, ethanol, dimethylformamide, dimethyl sulfoxide, glycerol and the like. They can be used singly or as a mixture. The preferable concentration of the organic solvent is about 0 to about 65%, especially about 40 to 60% of the reaction mixture. The ratio of the organic solvent should be determined by the solubility of starting materials, decline of enzyme to denature and its hydrolyzing activity. Ethanol, dimethylformamide and their mixture are preferably used, especially the mixture.

Reaction medium may be chosen from trishydroxymethylaminomethane (abbreviated tris hereinafter), carbonate, borate buffer solutions and the like. Enzyme concentration is determined depending on concentration of substrates and enzyme activity. For example, crystalline trypsin on the market is used preferably in a concentration from about 1 mg/ml to 10 mg/ml. Enzyme may be used intact or in a fixed form such as a combination with or an inclusion in insoluble carrier such as cellulose, dextran (e.g. Sephadex (trade mark)), agarose, (e.g. Sepharose (trade mark)), polyacrylamide gel (Bio-gel (trade mark)), porous glass and the like.

Reaction time is variable and is affected by other reaction conditions. Reaction may be continued until substrate and product reach equilibrium. It takes generally about 3 to 72 hours and in most cases about 6 to 24 hours.

The product insulin may be isolated by combining the usual method used in peptide chemistry. An isolation procedure is illustrated as follows: The reaction mixture is applied to gel filtration to isolate and collect unreacted Compound I and enzyme. The recovered Compound I and enzyme can be reutilized. The remaining part is applied to suitable chromatography to isolate a resultant protected-insulin and an unreacted des-B30-insulin. The latter can be reused as Compound II. The former is subjected to reaction for removal of the protecting group.

The removal of protecting group is effected according to the usual manner, though the method should be chosen depending on the properties of the protecting group. The t-butyl group is exemplified as a protecting group for both the hydroxy and carboxyl group of threonine. It may be removed by treating with trifluoroacetic acid in the presence of a cation-trapping agent, e.g. anisole. As noted above, if a sole treatment may remove the hydroxyprotecting and the carboxyl-protecting groups at once, the process becomes simple and results in good yield. When the C-terminal of the resultant insulin is protected with other ester, amide, substituted amide or salt, the protecting group may be removed by suitable hydrolysis or desalting technique.

The insulin prepared by this invention is useful for treatment of diabetes and also as a reagent.

The insulin obtained by this invention shows the same activity of lowering blood sugar level as bovine insulin in mice as follows:

Test Method: Test compound is dissolved in 0.01 M hydrochloric acid and the solution is diluted to a suitable concentration (2.5–20 μg/ml) with 20 to 60 times of physiological salt solution. The resultant solution is intravenously administered in a portion of 0.1 ml/10 g body weight to DS mice fasted for 5 hours. Blood is taken from orbital blood vessel 45 minutes after the administration and blood sugar is measured by glucose-oxidase method using a commercial kit produced by Boehringer Mannheim Corporation.

TABLE 1

| Test Compound | Insulin Activity Dose (μg/10 g Body Weight) | Blood Glucose Level (mg/dl) | |
|---|---|---|---|
| Physiological Salt Solution | — | 112.2 ± 7.3 | (1) |
| Semi-synthetic | 0.25 | 80.2 ± 2.6 | (2) |
| Human Insulin | 1 | 41.0 ± 6.0 | (3) |
| Bovine Insulin | 0.25 | 73.2 ± 1.5 | (4) |
|  | 1 | 41.0 ± 2.3 | (5) |

Note: (2)–(4), (3)–(5) No significant difference

Human insulin prepared by this invention can be administered to human beings in the same manner as porcine or bovine insulin preparations on the market. It may be made into pharmaceutical preparations in the usual manner. For example, it may be made into an injectable solution by a suitable procedure such as those for preparing zinc complex with zinc chloride, a buffered solution with a suitable buffer such as sodium hydrogenphosphate, sodium acetate and the like, and an isotonic solution with sodium chloride. Furthermore, suitable antiseptics may be added thereto. They are, for example, cresol, phenol, para-hydroxybenzoic acid alkyl esters (e.g. methyl, ethyl, propyl, butyl esters and the like). The dosage of the human insulin is the same as insulin preparations on the market. Namely, about 1 to 100 units may be administered to a human adult per day, though dosage depends on the seriousness of diabetes.

The following examples are given to further illustrate and describe the present invention. Each abbreviation has the meaning as follows: Ala: alanine, Arg: arginine, Asp: aspartic acid, CysO$_3$H: cysteic acid, Glu: glutamic acid, Gly: glycine, His:histidine, Ile: isoleucine, Leu: leucine, Lys: lysine, Phe: phenylalanine, Pro: proline, Ser: serine, Thr: threonine, Tyr: tyrosine, Val: valine, OBu$^t$: t-butyl ester residue.

EXAMPLE 1

(1) Desalanine-(B30)-porcine insulin

To a solution of porcine insulin (500 mg) in 0.1 M ammonium hydrogencarbonate (100 ml, pH 8.3) is added crystalline carboxypeptidase A (5 mg, Worthington Co., pretreated with diisopropylfluorophosphate, 49 u/mg). The mixture is incubated at room temperature for 8 hours. The incubation is stopped when alanine is released at a ratio of 0.77 M/1 M insulin. The reaction mixture is lyophilized. The product is dissolved in 0.5 M acetic acid and adsorbed on a column of Sephadex G 50 (3.5×95 cm) of super fine particles. The column is eluted with 0.5 M acetic acid with a portion of 11.5 ml per one fraction. Fraction Nos. 40–60 are collected and lyophilized to give the title compound (460 mg). Yield is 92%.

The product is hydrolyzed for amino acid analysis with 6 M hydrochloric acid at 110° C. for 24 hours to give the following result. The figures in the parenthesis show the theoretical values throughout this specification.

Amino acid analysis: Lys 1.00 (1), His 1.91 (2), Arg 0.95 (1), Asp 3.21 (3), Thr 2.09 (2), Ser 2.97 (3), Glu 7.35 (7), Gly 4.29 (4), Ala 1.26 (1), CysO$_3$H 5.94 (6), Val 3.86 (4), Ile 1.55 (2), Leu 6.53 (6), Tyr 4.08 (4), Phe 3.22 (3), Pro 1.2 (1).

(2) [B30-Thr-OBu$^t$]-porcine insulin

The above product (100 mg, 10 mM) and L-threonine t-butyl ester (205 mg, 500 mM) are dissolved in a mixture (1.05 ml) of ethanol and dimethylformamide (1:1, v/v). To the solution is added a solution of crystalline trypsin (4 mg, Worthington Co., recrystallized three times) in 0.5 M borate buffer solution (0.75 ml, pH 6.5) and TPCK in the final concentration of 0.01 mM. The mixture is kept overnight at 37° C. The product is confirmed with high precious liquid chromatography and the calculated yield is 75%. The mixture is acidified with glacial acetic acid and applied to gel filtration with a column of Sephadex G 50 (4.2×130 cm) of super fine particles to give three fractions corresponding to trypsin, the title insulin derivative and L-threonine t-butyl ester. Measurements of enzyme activity and Ninhydrin reaction reveals that trypsin and L-threonine t-butyl ester are recovered in an amount of 50%, respectively.

The fraction containing the insulin derivative is lyophilized to yield a crude powder (89 mg) of the title compound. The product is applied at 4° C. to a column of DEAE-Sephadex A 25 (1.9×24.5 cm) which is previously equilibrated with 0.01 M tris buffer solution (pH 7.6) and 7 M urea. The column is eluted with the above buffer solution (800 ml) and then a linear Na$^+$ gradient (to 0.3 M NaCl) is performed to give a fraction A near 0.08 to 0.09 M concentration and a fraction B near 0.13 to 0.14 M. Each fraction is immediately dialyzed against 0.01 M ammonium acetate for 3 to 4 days in a cool place and lyophilized to give a powder (35 mg) from the fraction A and a powder (27 mg) from the fraction B. The former is identified to be the title compound and the latter is identified to be a mixture of desalanine-(B30)-porcine insulin and intact porcine insulin by high precious liquid chromatography and polyacrylamide gel electrophoresis.

(3) Human insulin

Trifluoroacetic acid (2 ml) with anisole (0.2 ml) is added to the product (30 mg) obtained above and the mixture is kept at room temperature for 30 minutes. The trifluoroacetic acid is removed under nitrogen atmosphere and the mixture is extracted with ether (15 ml) after addition of 1 N acetic acid (2 ml) to remove the anisole. The acetic acid layer is lyophilized to give the title compound (28 mg). Yield is 43% when calculated from the starting compound 77% purity.

The product is identified as the title compound by amino acid analysis, Slab gel electrophoresis and high precious liquid chromatography. Amino acid analysis is performed under the same condition as in (1) and the result is as follows: Amino acid analysis: Lys 1.00 (1), His 1.89 (2), Arg 0.87 (1), Asp 3.32 (3), Thr 3.16 (3), Ser 2.99 (3), Glu 7.35 (7), Pro 1.29 (1), Gly 4.39 (4), Ala 1.26 (1), CysO$_3$H 4.6 (6), Val 3.93 (4), Ile 1.61 (2), Leu 6.51 (6), Tyr 3.68 (4), Phe 3.19 (3).

EXAMPLE 2

(1) Desalanine-(B30)-bovine insulin

To a solution of bovine insulin (200 mg) in 0.1 M ammonium hydrogencarbonate (40 ml) is added crystalline carboxypeptidase A (1.8 mg, 49 u/mg). The mixture is kept overnight at room temperature and lyophilized to give a crude powder (180 mg) of the above title compound. The product is assured to consist of 78% of the title compound and 22% of desasparagine-(A21)-desalanine-(B30)-insulin.

(2) [B30-Thr-OBu$^t$]-bovine insulin

The product (116 mg, 5 mM) obtained above in (1) and L-threonine t-butyl ester (448 mg, 500 mM) are dissolved in a mixture (2.4 ml) of ethanol and dimethylformamide (1:1). The solution is mixed with 0.5 M borate buffer solution (1.6 ml, pH 7.0) containing crystalline trypsin (87.5 mg, 0.94 mM) and TPCK (0.27 mg, 0.2 mM) and incubated overnight at 37° C. The production of the title compund is confirmed by high precious liquid chromatography and the yield is calculated to be 80%.

The reaction mixture is treated in the same manner as in Example 1 (2). The resultant fraction A is re-chromatographed to remove desasparagine-(A21)-desalanine-(B30)-insulin and treated in the same manner as in Example 1 (2) to give a crude powder (63 mg). The product is identified to be the title compound by high precious liquid chromatography and Slab gel electrophoresis.

(3) [B30-Thr]-bovine insulin

To the product (63 mg) obtained above in (2) is added trifluoroacetic acid (2 ml) with anisole (0.2 ml). The mixture is kept at room temperature for 30 minutes, then treated in the same manner as in Example 1 (3) and lyophilized to give the title compound (60 mg). Yield is 66% when calculated from the starting compound 78% purity.

The product is identified with [B30-Thr]-bovine insulin prepared by other method by amino acid analysis, Slab gel electrophoresis and high precious liqud chromatography. Amino acid analysis is performed under the same condition as in Example 1 (1) and the result is as follows: Amino acid analysis: Lys 1.00 (1), His 1.95 (2), Arg 0.98 (1), Asp 3.00 (3), Thr 2.00 (2), Ser 2.83 (3), Glu 6.69 (7), Gly 4.06 (4), Ala 2.06 (2), CysO₃H 5.38 (6), Val 4.45 (5), Ile 0.76 (1), Leu 6.14 (6), Tyr 3.92 (4), Phe 2.97 (3), Pro 1.20 (1).

What is claimed is:

1. A process for preparing a B30-threonine-insulin which comprises converting an animal insulin to a des-B30-insulin, reacting the des-B30-insulin with a threonine derivative of the formula.

$$Thr(R^1)(R^2)$$

wherein Thr is an L-threonine residue, $R^1$ is hydrogen or a hydroxy-protecting group and $R^2$ is a carboxyl-protecting group, in a molar ratio of the threonine derivative to the des-30-insulin of 5:1 to 1000:1, and in the presence of an enzyme specifically acting on the basic-amino-acid carbonyl in peptide bondings selected from the group consisting of trypsin, a trypsin-like enzyme produced by *Streptomyces fradiae* ATCC 3535 and a trypsin-like enzyme produced by *Streptomyces erythreus*, and subjecting the resultant product to one or more reactions to remove all of the protecting groups.

2. The process according to claim 1, wherein the reaction is carried out in the presence of trypsin.

3. The process according to claim 1, wherein the molar ratio of the threonine derivative to the des-B30-insulin is about 25:1 to 200:1.

4. The process according to claim 1, wherein the molar ratio of the threonine derivative to the des-B30-insulin is about 20:1 to 100:1.

5. The process according to claim 1, wherein the B30-threonine-insulin is human insulin, and the animal insulin is porcine insulin.

6. The process according to claim 1 or 2, wherein the reaction is effected in a medium containing one or more water-miscible organic solvents.

7. The process according to claim 6, wherein the organic solvent is selected from the group consisting of methanol, ethanol, dimethylformamide, dimethyl sulfoxide and glycerol.

8. The process according to claim 7, wherein the organic solvent is selected from the group consisting of ethanol and dimethylformamide.

9. A process for preparing a protected B30-threonine-insulin which comprises converting an animal insulin to a des-B30-insulin, and reacting the des-B30-insulin with a threonine derivative of the formula $$Thr(R^1)(R^2)$$

wherein Thr is an L-threonine residue, $R^1$ is hydrogen or a hydroxy-protecting group and $R^2$ is a carboxyl-protecting group, in a molar ratio of the threonine derivative to the des-B30-insulin of 5:1 to 1000:1, and in the presence of an enzyme specifically acting on the basic-amino-acid carbonyl in peptide bondings selected from the group consisting of trypsin, a trypsin-like enzyme produced by *Streptomyces fradiae* ATCC 3535 and a trypsin-like enzyme produced by *Streptomyces erythreus*.

10. The process according to claim 9, wherein the reaction is carried out in the presence of trypsin.

11. The process according to claim 9, wherein the molar ratio of the threonine derivative to the des-B30-insulin is about 25:1 to 200:1.

12. The process according to claim 9, wherein the molar ratio of the threonine derivative to the des-B30-insulin is about 20:1 to 100:1.

13. The process according to claim 9, wherein the protected B30-threonine-insulin is a protected human insulin, and the animal insulin is porcine insulin.

14. The process according to claim 1 or 9, wherein the des-B30-insulin is des-B30-porcine-insulin.

15. The process according to claim 1 or 9, wherein the des-B30-insulin is des-B30-bovine insulin.

16. The process according to claim 1 or 9, wherein the threonine derivative is L-threonine t-butyl ester.

17. The process according to claim 1 or 9, wherein the reaction is effected at pH 5 to pH 9.

18. The process according to claim 17, wherin the reaction is effected at pH 6 to pH 7.

19. The process according to claim 1 or 9, wherein the reaction is effected at a temperature of 0° to 50° C.

20. The process according to claim 19, wherein the reaction is effected at a temperature of 20° to 40° C.

* * * * *